(12) United States Patent
Tague et al.

(10) Patent No.: US 6,796,987 B2
(45) Date of Patent: Sep. 28, 2004

(54) DELIVERY DEVICE FOR BONE CEMENT

(75) Inventors: Christopher M. Tague, Portage, MI (US); Dennis A. Stratton, Plainwell, MI (US); James G. Walen, Kalamazoo, MI (US); Richard F. Huyser, Kalamazoo, MI (US)

(73) Assignee: Stryker Instruments, Kalamazoo, MI (US)

( * ) Notice: Subject to any disclaimer, the term of this patent is extended or adjusted under 35 U.S.C. 154(b) by 0 days.

(21) Appl. No.: 10/167,018

(22) Filed: Jun. 11, 2002

(65) Prior Publication Data

US 2003/0109884 A1 Jun. 12, 2003

Related U.S. Application Data

(63) Continuation-in-part of application No. 09/906,455, filed on Jul. 16, 2001, now Pat. No. 6,599,293.
(60) Provisional application No. 60/327,451, filed on Oct. 5, 2001.

(51) Int. Cl.[7] ............................. A61B 17/58; A61F 2/00
(52) U.S. Cl. ......................................... 606/94; 222/390
(58) Field of Search .............................. 606/92, 93, 94; 604/211, 224, 232, 234; 222/226, 390

(56) References Cited

U.S. PATENT DOCUMENTS

| | | | |
|---|---|---|---|
| 949,163 A | * 2/1910 | Stapley | 222/390 |
| 1,612,996 A | 1/1927 | Waagbo | |
| 2,745,575 A | * 5/1956 | Spencer | 222/327 |
| 2,874,877 A | * 2/1959 | Spencer | 222/162 |
| 3,144,966 A | 8/1964 | Cook | |
| 3,216,616 A | 11/1965 | Blankenship, Jr. | |
| 3,217,946 A | 11/1965 | Cook | |
| 3,459,341 A | 8/1969 | Copeland | |
| 3,873,008 A | * 3/1975 | Jahn | 222/390 |
| 4,189,065 A | * 2/1980 | Herold | 222/46 |
| 4,269,331 A | * 5/1981 | Watson | 222/390 |
| 4,371,094 A | 2/1983 | Hutter, III | |
| 4,583,974 A | * 4/1986 | Kokernak | 604/211 |
| 4,832,692 A | * 5/1989 | Box et al. | 604/99.01 |
| 5,306,248 A | * 4/1994 | Barrington | 604/97.02 |
| 5,308,340 A | * 5/1994 | Harris | 604/208 |
| 5,829,875 A | 11/1998 | Hagel et al. | |
| 6,599,293 B2 | * 7/2003 | Tague et al. | 606/94 |

* cited by examiner

Primary Examiner—Ralph A. Lewis
(74) Attorney, Agent, or Firm—Howard & Howard

(57) ABSTRACT

A delivery apparatus for injecting cement from a cartridge includes a cradle, a cartridge, a button, and a threaded rod. The cradle has an axial cavity extending therethrough for supporting the cartridge of cement. The cartridge dispensing mechanism is coupled to the cradle. The button includes threads and defines an axial bore. The button is moveable into and out of threaded engagement with the threaded rod. The threaded rod extends into the axial cavity of the cradle.

30 Claims, 9 Drawing Sheets

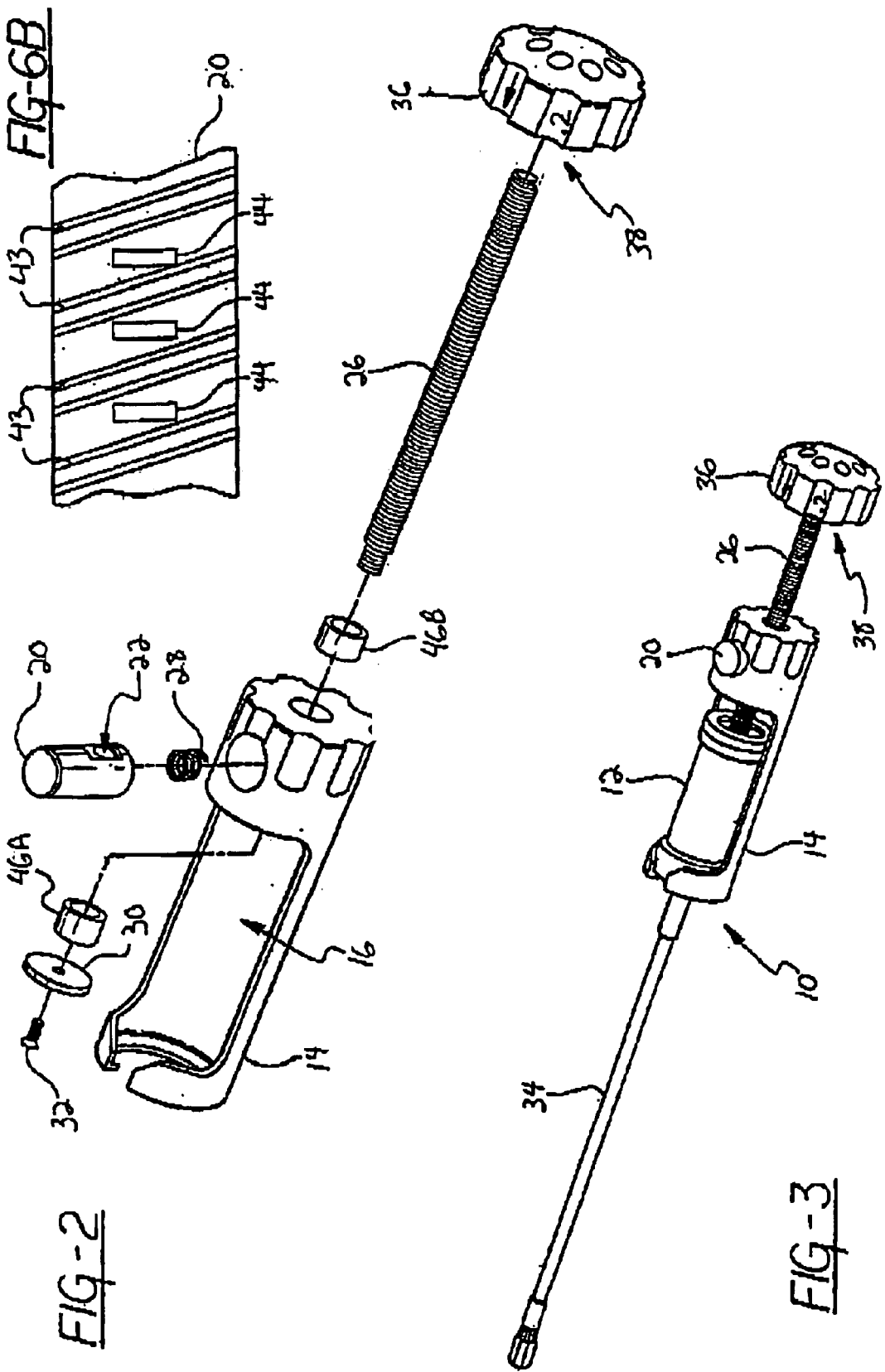

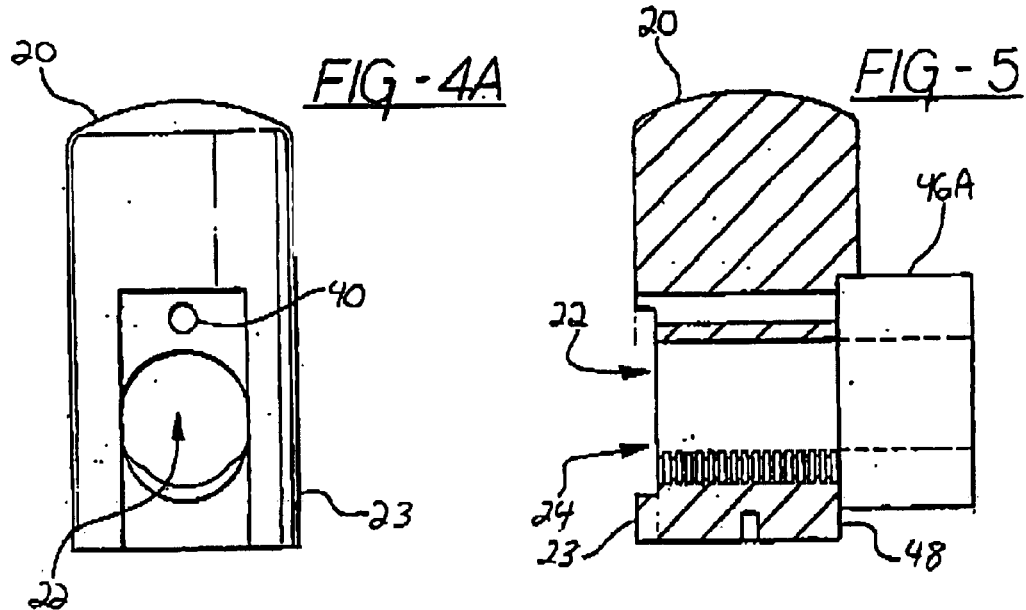
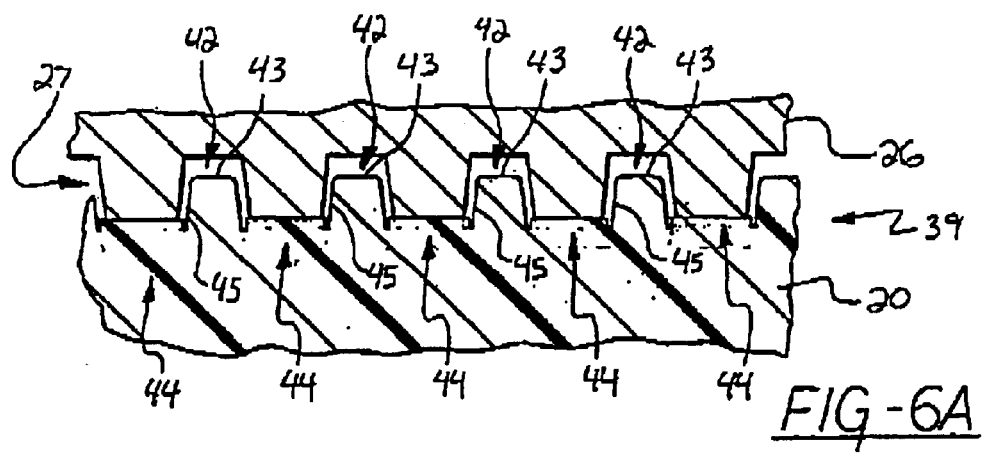
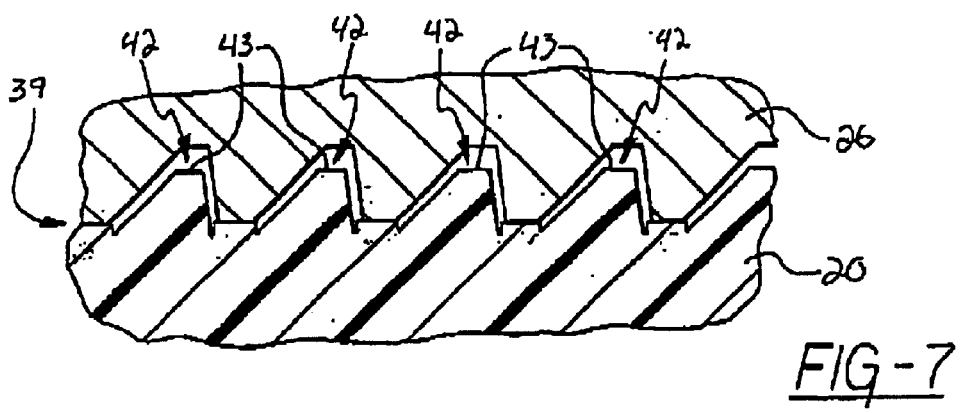

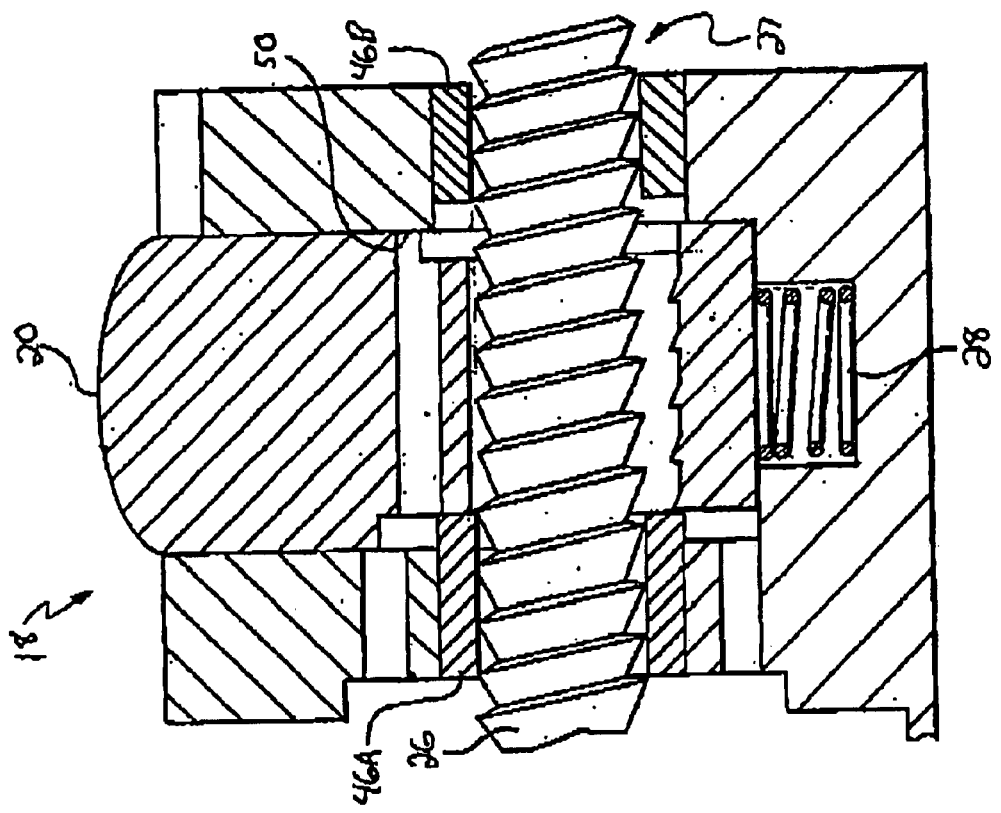
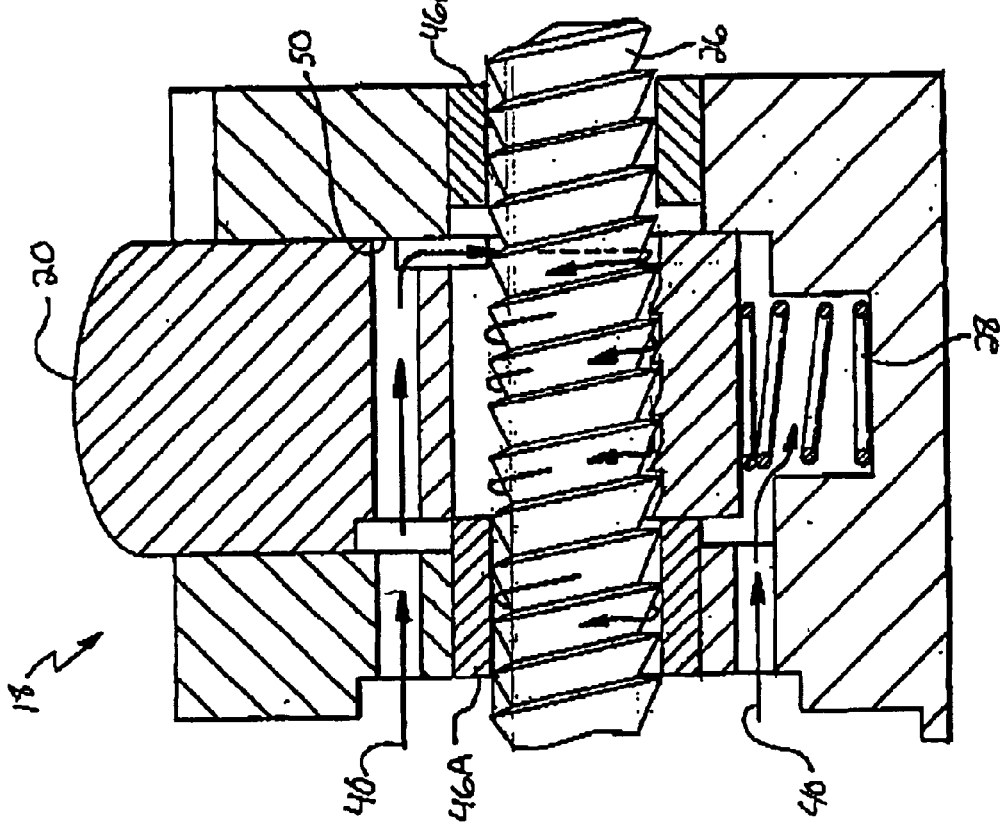

FIG-17
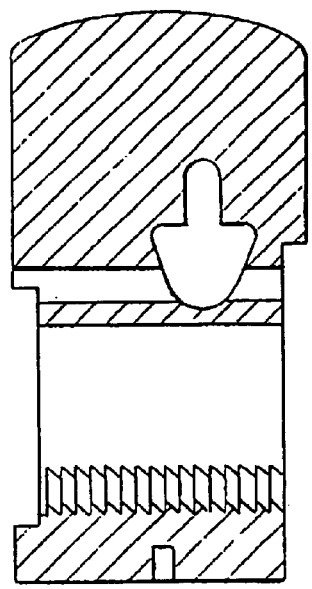
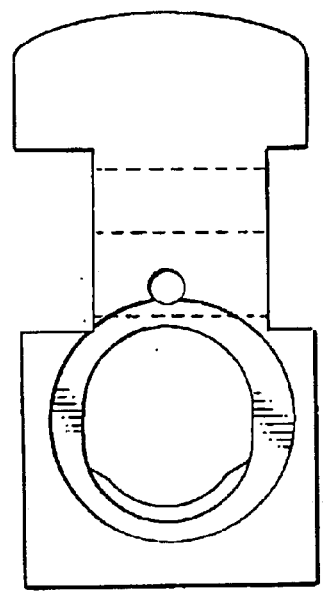
FIG-18
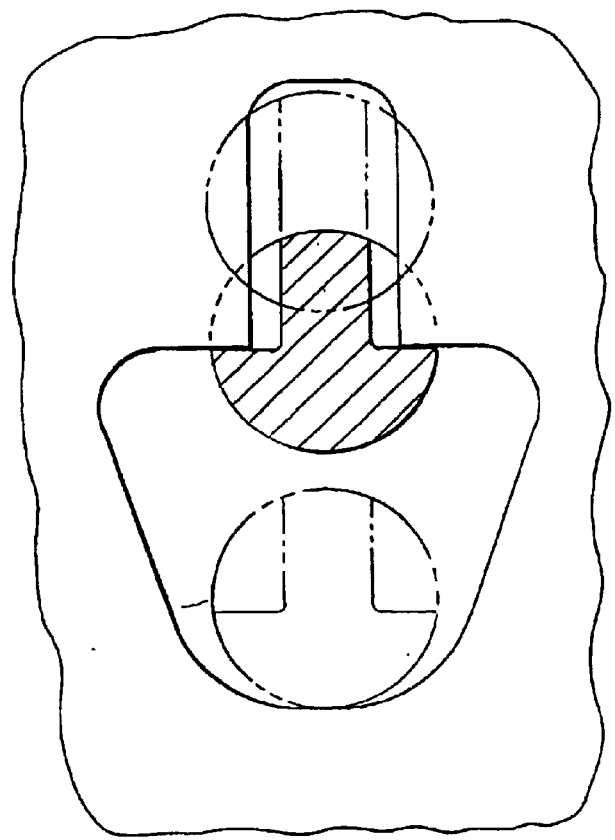
FIG-19

DELIVERY DEVICE FOR BONE CEMENT

CONTINUATION-IN-PART APPLICATION

This application is a continuation-in-part of U.S. application Ser. No. 09/906,455 filed Jul. 16, 2001, now U.S. Pat. No. 6,599,293 issued Jul. 29, 2003.

CROSS-REFERENCE TO RELATED APPLICATIONS

This application claims the benefit of U.S. Provisional Patent Application Serial No. 60/327,451 filed Oct. 5, 2001.

FIELD OF THE INVENTION

The invention generally relates to a delivery apparatus for bone cement and, in particular, to a bone cement delivery device that uses a dispensing mechanism for quickly priming the delivery apparatus and delivering the bone cement.

BACKGROUND OF THE INVENTION

The necessity to apply bone cement to a bone during surgical procedures, such as the attachment of a prosthesis or pathological fracture fixation, has been well known in the surgical community. With regard to the attachment of a prosthesis, the cement is packed into the bone and the prosthesis is then attached. The cement cures and a bond develops between the bone and the prosthesis. Traditionally, surgeons have packed the bone cement into the bone by hand. A disadvantage to that technique is that often a weak bond develops between the bone and the prosthesis. When packing the cement by hand the surgeon unknowingly applies insufficient pressure and the cement fails to properly penetrate the bone, thereby creating a weaker bond. Additional disadvantages of packing the cement by hand include excessive time consumption and often the quickly curing cement hardens before the surgeon has finished packing the cement.

Other uses of bone cement include repairing or mending bone fractures or shattered bone occurring from extreme trauma. Bone cement may also be used during cosmetic or dental surgery. Moreover, bone cement may be used as a drug delivery or release system, whereby the bone cement is mixed with antibiotics or other desired drugs and applied to a specific surgical site such that the drugs leach out and are delivered directly to the surgical site. Some bone cements are also designed to be absorbed by the body over time.

To overcome some of these disadvantages, delivery apparatuses have been developed to apply the cement to the bone. One such apparatus greatly resembles a common household caulking gun with a cartridge of caulk. This prior art apparatus has a pistol-shaped body which supports a cartridge of bone cement. The apparatus includes a ram actuated by a movable trigger for pushing the cement out of the cartridge and through a nozzle. A pull of the trigger advances a rod that also advances the ram. The prior art delivery apparatuses also provide structures for adjusting the dispensed quantity of cement per trigger pull. Traditionally this adjustment is accomplished by preventing the full actuation of the trigger with a mechanical stop. The resulting quantity of dispensed cement after the mechanical adjustment is often an imprecise calculation. Additionally, the apparatus delivers a discrete amount of cement per "tooth" of the ram.

The prior art dispensing apparatus have many disadvantages. First, to advance the ram during an initial loading of the cartridge of cement the trigger must be actuated repetitively. This is a very time consuming step during a complex orthopedic surgery. Additionally, a bone cement delivery apparatus must be sterilized prior to being admitted into an operating room. Often the compact design of the delivery apparatus' cartridge dispensing mechanism or trigger assembly makes sterilization in a traditional autoclave unit difficult because the steam is unable to properly penetrate the components of the apparatus.

Currently, there is a need for a delivery apparatus for bone cement with a simple, yet effective design that allows surgeons to quickly prime the apparatus when loading a new cartridge of cement, non-discretely dispensing cement, and properly sterilizing the apparatus.

SUMMARY OF THE INVENTION AND ADVANTAGES

In one aspect of the present invention, a delivery apparatus for injecting cement from a cartridge, is provided having a cradle with an axial cavity extending therethrough for supporting the cartridge, a cartridge dispensing mechanism coupled to the cradle and defining a cylindrical bore therein, a button having threads and defining an axial bore, a keyed bore disposed in the button and being linearly aligned with the cylindrical bore, a threaded rod in threaded engagement with the axial bore of the button and extending into the axial cavity of the cradle wherein the button is moveable into and out of threaded engagement with the threaded rod, and a locking pin slideably disposed in both the cylindrical bore and the keyed bore for being moved from a first position to a second position.

In another aspect of the present invention, a delivery apparatus for injecting cement from a cartridge is provided having a cradle with an axial cavity extending therethrough for supporting the cartridge, a cartridge dispensing mechanism coupled to the cradle and defining a cylindrical bore therein, a button having threads and defining an axial bore, a keyed bore disposed in the button and being linearly aligned with the cylindrical bore, a threaded rod in threaded engagement with the axial bore of the button and extending into the axial cavity of the cradle wherein the button is moveable into and out of threaded engagement with the threaded rod, a locking pin slideably disposed in both the cylindrical bore and the keyed bore for being moved from a first position to a second position, a first cleaning passageway defined by the cartridge delivery mechanism and extending from the exterior thereof to the threaded engagement of the rod, threads disposed in the axial bore and being spaced from the threaded rod to define a second cleaning passageway for convey a cleaning medium therethrough, a biasing device for biasing the threads of the axial bore into threaded engagement with the threaded rod, a limiting structure for limiting travel of the button and minimizing friction and pinching between the button and the threaded rod, and bushings slidably supporting the threaded rod.

BRIEF DESCRIPTION OF THE DRAWINGS

Other advantages of the present invention will be readily appreciated as the same becomes better understood by reference to the following detailed description when considered in connection with the accompanying drawings wherein:

FIG. 2 is an exploded perspective view of the delivery apparatus of the subject invention;

FIG. 3 is a perspective view of the delivery apparatus containing a cartridge of bone cement and includes a nozzle;

FIG. 17 is a cross-sectional view of a button, according to the embodiment of FIG. 10;

FIG. 18 is a side view of the button of FIG. 17;

FIG. 19 is a cross-sectional view of the button of FIG. 17;

DETAILED DESCRIPTION OF TEE PREFERRED EMBODIMENT

Figure 1:
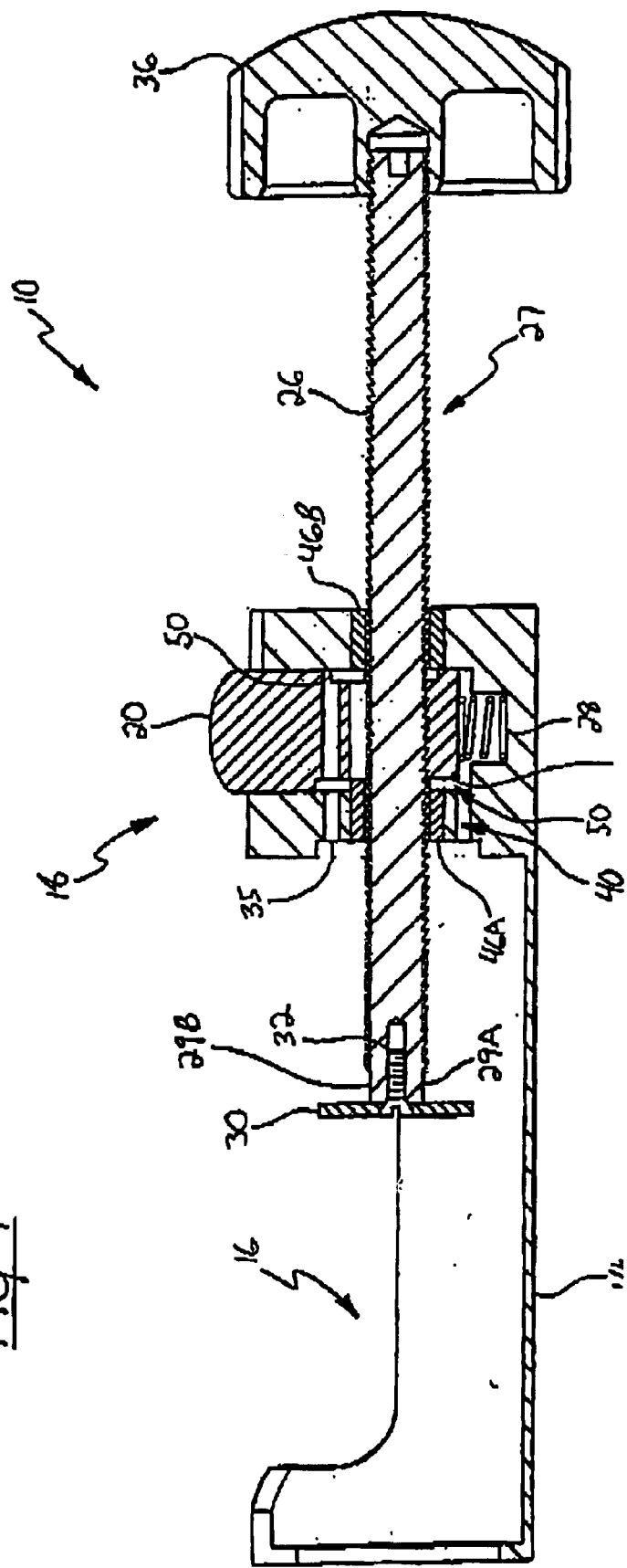
FIG. 1 is a cross-sectional view of a delivery apparatus of the subject invention.

Referring to the Figures, wherein like numerals indicate like or corresponding parts throughout the several views, a delivery apparatus is generally shown at 10 in FIG. 1. The delivery apparatus 10 is used to deliver bone cement from a cartridge 12 to a patient. The cement is applied to bone of the patient to create a bond between the bone and a prosthesis or to fuse a fracture. The delivery apparatus 10 comprises a cradle 14 having an axial cavity 16 extending therethrough. The cradle 14 supports the cartridge 12 of cement in the axial cavity 16. In one embodiment, the cradle 14 is a quick load type cradle, as shown. The quick load cradle 14 includes a semi-open body with a unitarily constructed endcap. In another embodiment, the cradle is substantially enclosed and has a removable endcap.

In one embodiment, delivery of the bone cement is performed percutaneously. Percutaneous, as used in the medical field, relates to passing or effectuating the bone cement through the skin.

Figure 4B:
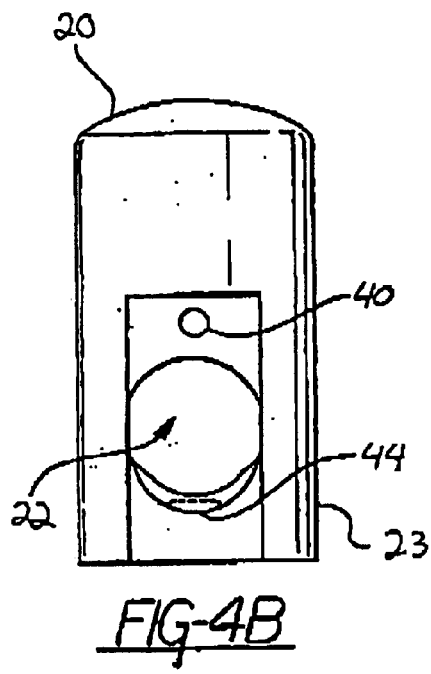
FIG. 4 is an end view of a button of a cartridge dispensing mechanism of the delivery apparatus of FIG. 1.
Figure 4A:
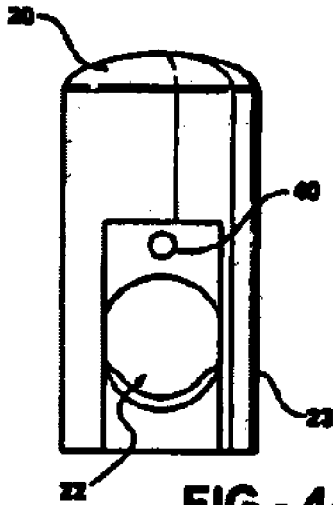
Figure 4B:
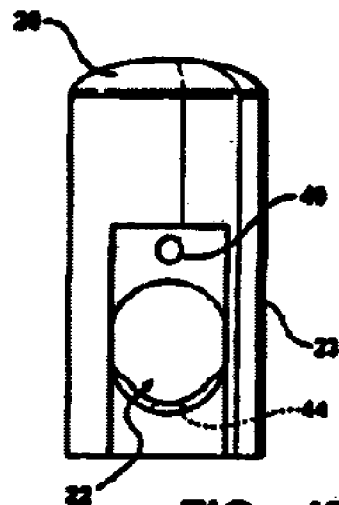
Figure 5:
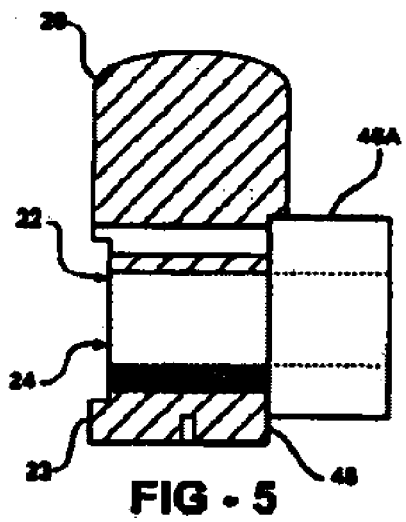
FIG. 5 is a cross-sectional view of the button of the cartridge dispensing mechanism of FIG. 4.

The cradle 14 also supports a cartridge dispensing mechanism generally indicated at 18. The mechanism 18 includes a button 20. In the preferred embodiment, a shown in FIGS. 2, 4 and 5, the button 20 has a generally cylindrical peripheral surface. An axial bore 22 is disposed through and formed by the button 20 and the dispensing mechanism 18. A bottom portion 23 of the axial bore 22 within the button 20 includes threads 24. The threads 24 engage a threaded rod 26 disposed through the axial bore 22. The threaded rod 26 includes a plurality of threads 27. With movement of the button 20, the threads 24 are disengaged from the threads 27 of the threaded rod 26. To permit disengagement, the axial bore 22 has a diameter larger than the diameter of the threaded rod 26.

The threads 24 of the button 20 are moveable into and out of engagement with the rod 26. A biasing device 28 is attached to a terminal end of the button 20. The biasing device 28, in the preferred embodiment, is a compression spring 28. In the absence of an external compressive force, the spring 28 will bias the threads 24 of the axial bore 22 into threaded engagement with the rod 26. To disengage the threads 24 from engagement with the rod 26, an operator must apply a downward compressive force on the top of the button 20. While disengaged, the threaded rod 26 may freely slide through the axial bore 22 to quickly advance the rod 26 into contact with the cartridge 12. This technique is known as priming of the delivery apparatus 10.

One end of the threaded rod 26 includes a disc 30. The disc 30 is attached to the end of the rod 26 with a fastener 32. With the button 20 depressed, the apparatus 10 is primed and the rod 26 and disc 30 are advanced into contact with the cartridge 12. The disc 30 penetrates one end of the cartridge 12 to eject the cement into a nozzle 34. The cement is ejected through the nozzle 34.

For percutaneous delivery, a flexible extension tube (not shown) is removably coupled to the nozzle 34. A needle having a handle (not shown) is coupled to the extension tube for injection through the skin and into the patient. The cement flows through the nozzle 34, extension tube, and needle and into the patient.

Additionally, the cartridge dispensing mechanism 18 includes a recess 35 for receiving the disc 30 when retracted.

The opposite end of the rod 26 includes a handle 36. When the threaded rod 26 is in engagement with the threads 24 of the axial bore 22, the handle 36 is manually rotated to advance the rod 26 and disc 30. This manual rotation dispenses a continuous amount of cement. Advancement of the rod rotationally is used during a surgical procedure to continuously deliver the amount of cement dispensed into the bone of the patient. Preferably, the rod 26 includes first and second flat surfaces 29A, 29B. The flat surfaces are adapted to receive a torque wrench (not shown) to facilitate installation of the handle 36.

In one embodiment, to assist the operator with dispensing a proper amount of cement, the handle 36 includes markings 38. The markings 38 are used to indicate the degree of rotation of the handle 36 and the amount of cement ejected. Rotation of the handle 36 from a first mark to a second mark indicates that the apparatus 10 has ejected a predetermined amount of cement. These markings 38 help guide the operator when using the apparatus 10. For example, as shown in FIGS. 2 and 3, a start position is indicated by an arrow marking on the handle 36. After priming, the arrow may be aligned with a corresponding marking on the cradle by pushing the button 20 down and rotating the handle 36. Thereafter rotation of the handle a portion of its full rotation, e.g., ⅛, delivers a predetermined amount of cement, e.g., 0.2 cc.

Figure 8:
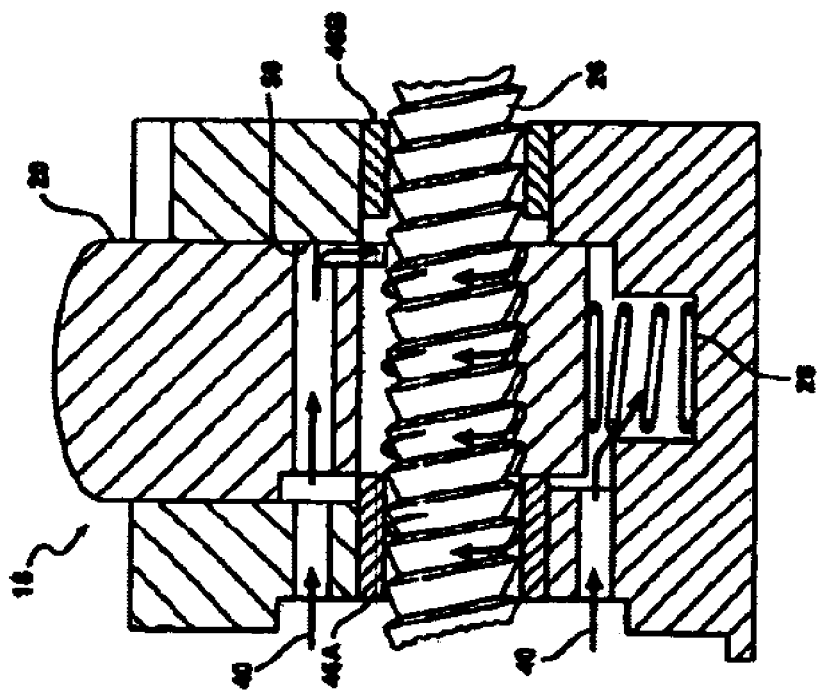
FIG. 8 is a cross-sectional view of the cartridge dispensing mechanism with the threaded rod engaged with the threads of the button.

The cartridge dispensing mechanism 18 defines a first cleaning passageway 40. The passageway 40 extends from the exterior of the mechanism 18 to the threaded engagement of the rod 26. The passageway 40 receives steam during a sterilization process in an autoclave unit. The steam penetrates the mechanism 18 through the passageway 40, as best shown in FIG. 8. The first cleaning passageway 40 assists in ensuring a properly sterilized apparatus 10 suitable for use in an operating room.

The threads 24 of the axial bore 22 of the button 20, while in engagement with the rod 26, also need to receive the steam during sterilization. To accomplish this feat, a second cleaning passageway 42 is created between the threads 24 of the bore 22 and the threaded rod 26. In the preferred embodiment, the threads 24 of the bore 22 are axially spaced from the threaded rod 26 to define the second cleaning passageway 42. The second cleaning passageway 42 allows steam to enter during the sterilization process.

Figure 6C:
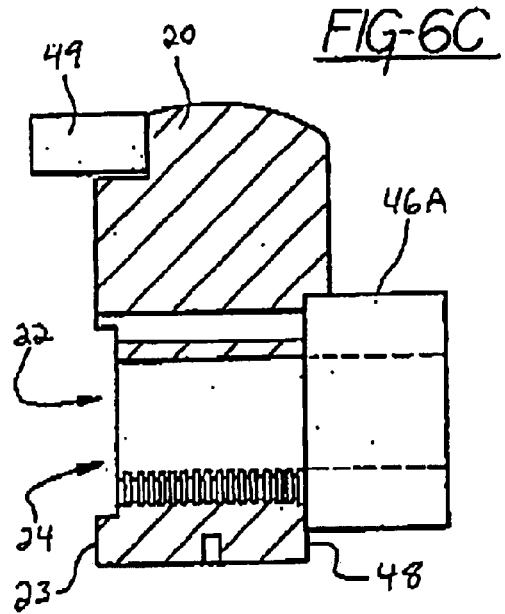
FIG. 6C is a perspective of a portion of the threads of FIG. 6A.

The threads 24 of the axial bore 22 and the rod 26 are axially spaced by a limiting structure 39. In one embodiment, as shown in FIGS. 6A–6C, the limiting structure 39 includes a horizontal base or shelf 44 located in the threads 24 of the axial bore 22. Preferably as shown in FIG. 6B, the horizontal base 44 only extends over a portion of a width of the button 20. Preferably, the threads 43 and the horizontal based 44 are formed simultaneously using an electronic discharge machining process.

The horizontal base 44 prevents the threaded rod 26 from fully penetrating the threads 24 of the axial bore 22. When the button 20 is not being pressed and is therefore biased into engagement with the rod 26, a top edge of the threads 27 of the rod 26 rests along a corresponding horizontal base 44. The horizontal base 44 helps minimize friction or pinching between the threads 24, 27 of the button 20 and the rod 26. As a result, the rotation and advancement of the rod 26 are easier for the operator.

Figure 6D:
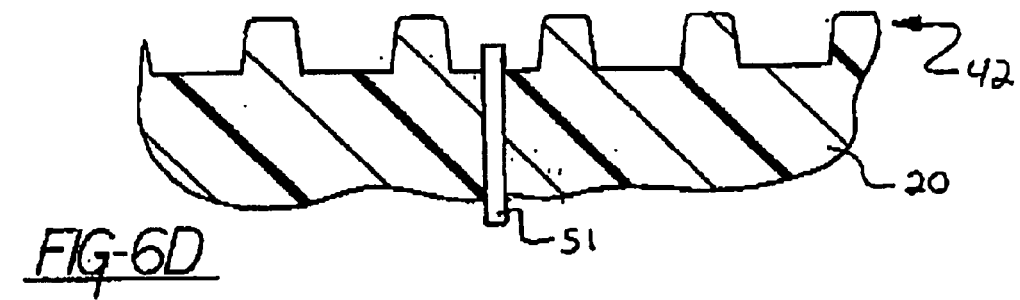
FIG. 6D is a portion view of a button with a stop according to an embodiment of the present invention.

In another embodiment as shown in FIG. 6D, the limiting structure 39 includes a stop 49 which limits the travel of the button, thereby minimizing friction and pinching.

Figure 6E:
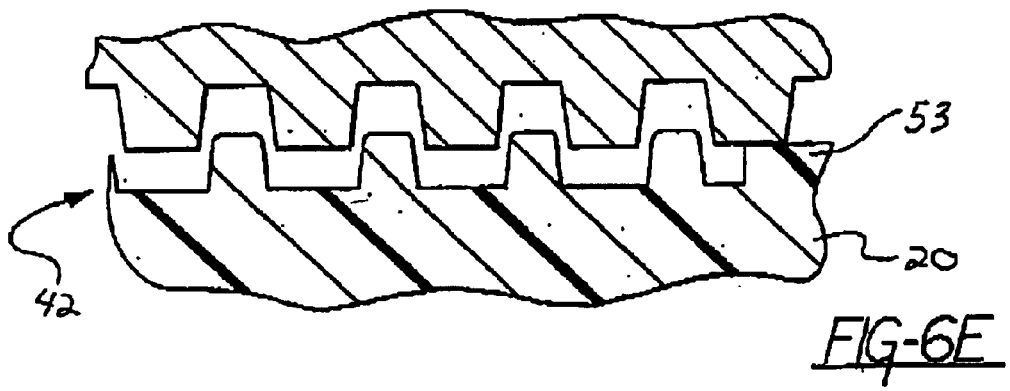
FIG. 6E is a perspective view of a portion of a button with a pin.
Figure 12:
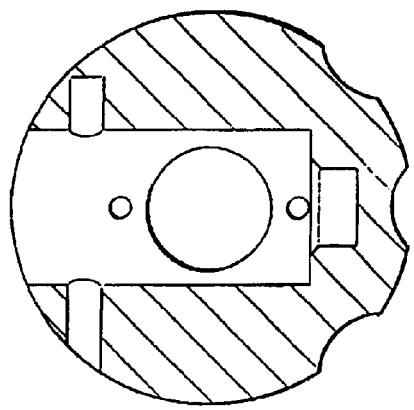
FIG. 12 is an exploded cross-sectional frontal view of the cartridge dispensing mechanism of FIG. 10.
Figure 10:
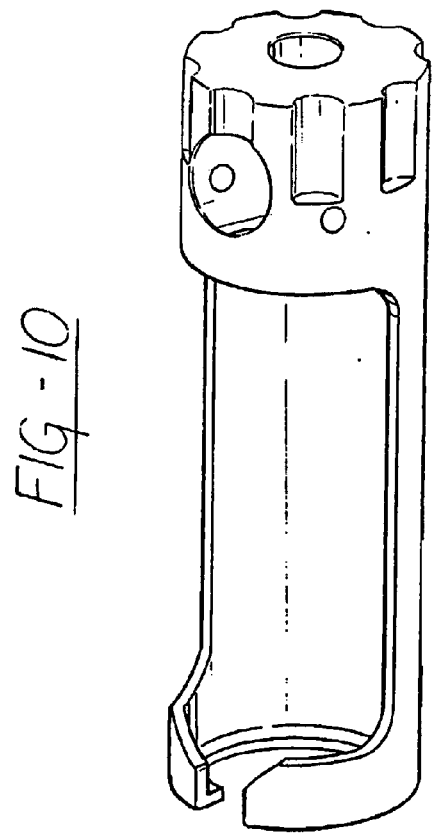
FIG. 10 is a perspective view of the cartridge dispensing mechanism, according to another embodiment of the present invention.
Figure 11:
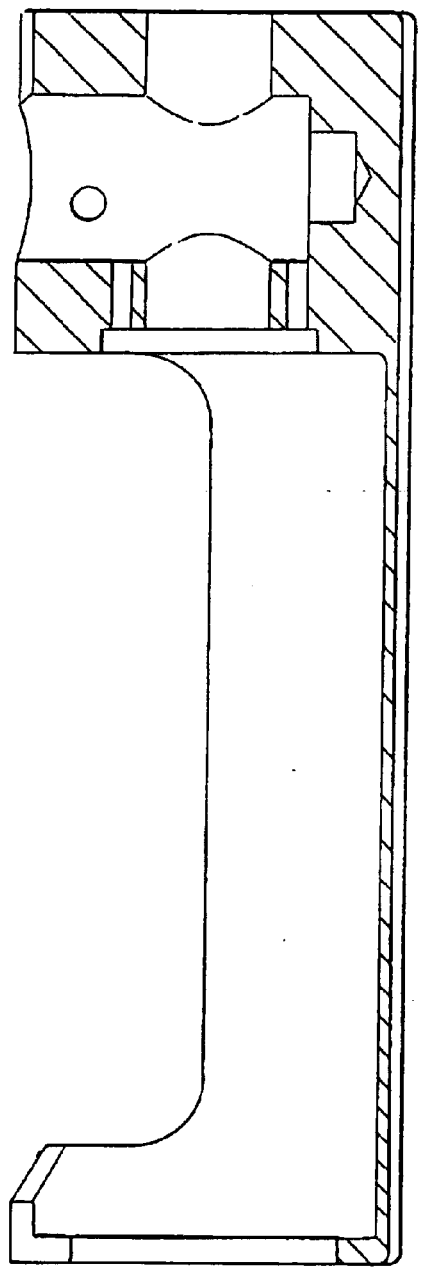
FIG. 11 is an exploded cross-sectional side view of the cartridge dispensing mechanism of FIG. 10.
Figure 13:
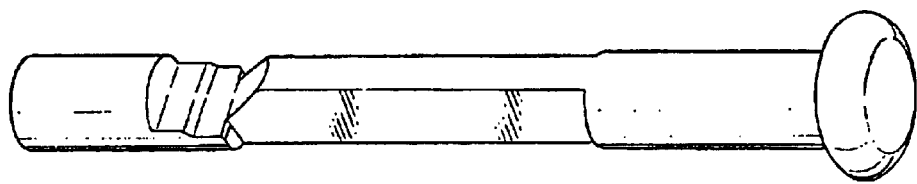
FIG. 13 is an exploded perspective view of a locking pin, according to the embodiment of FIG. 10.
Figure 14:
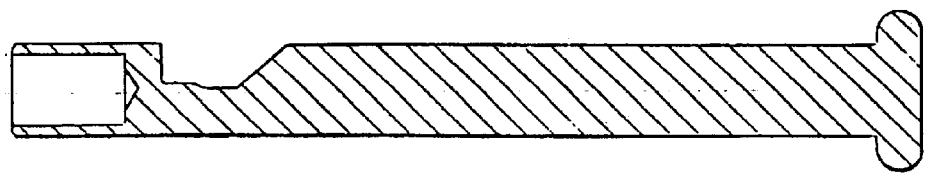
FIG. 14 is a cross-sectional side view of the locking pin of FIG. 13.
Figure 15:
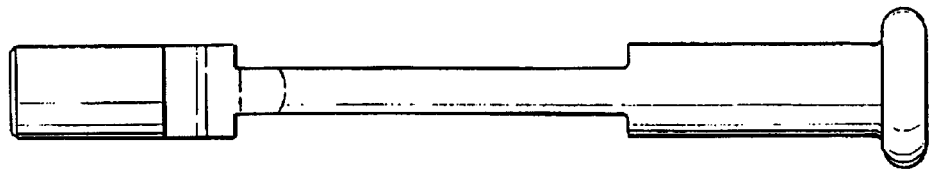
FIG. 15 is a top view of the locking pin of FIG. 13.
Figure 16:
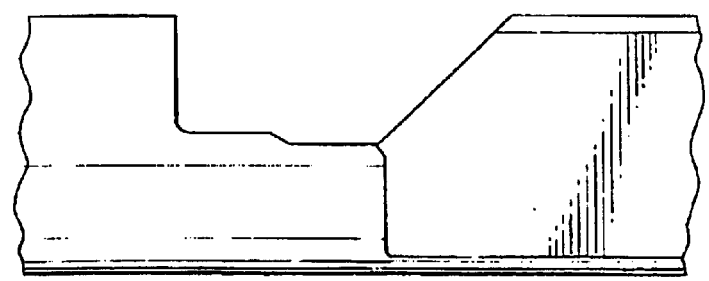
FIG. 16 is a side view of the shelf end of the locking pin of FIG. 15.
Figure 6B:
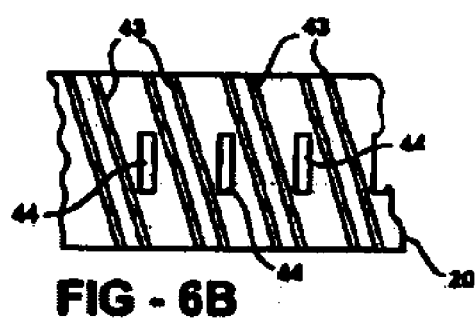
FIG. 6B is a top-down view of the threaded rod of FIG. 6B, according to an embodiment of the present invention.
Figure 6A:
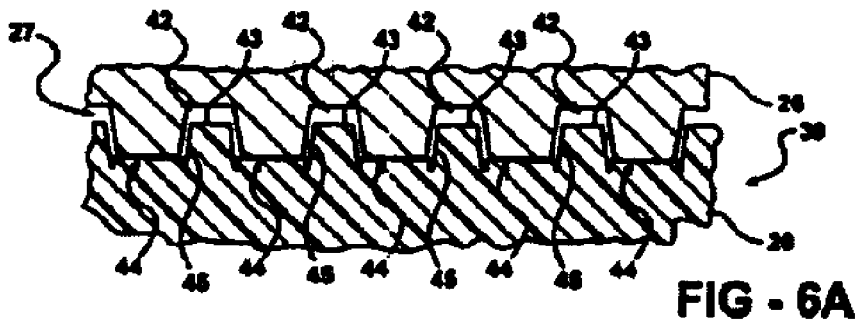
FIG. 6A is an enlarged perspective view of one embodiment of threads of the button of FIG. 4 in engagement with a threaded rod.
Figure 6C:
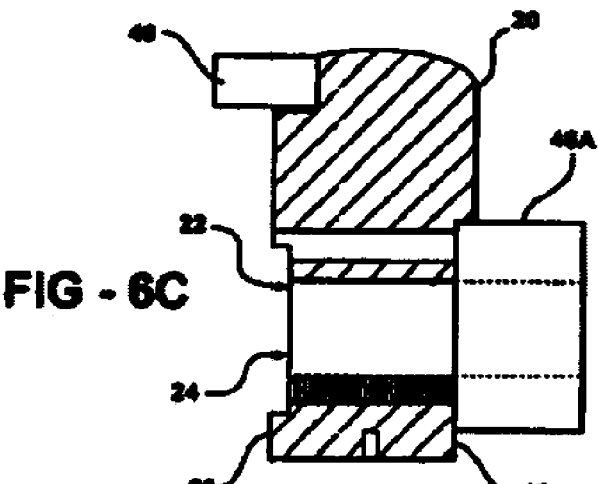
Figure 6D:
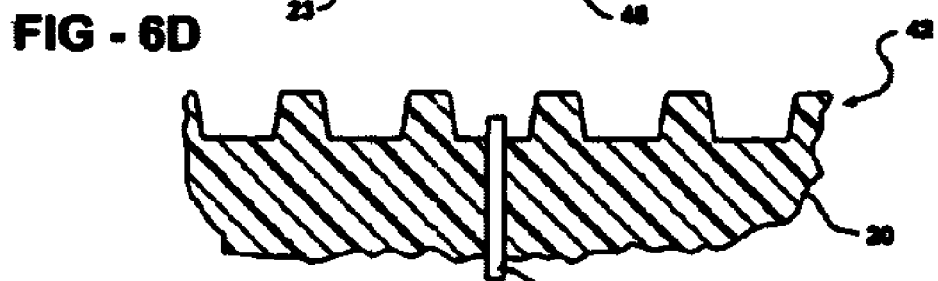
Figure 6E:
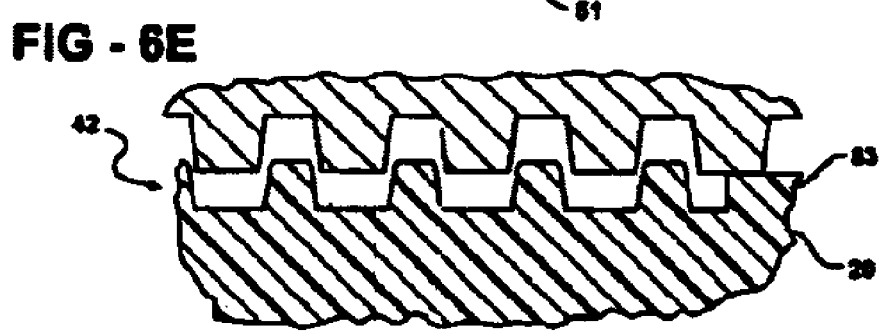

In still another embodiment as shown in FIG. 6E, the limiting structure 39 includes one or more pins 51 inserted through the bottom of the button 20 between the threads 24.

In yet still another embodiment as shown in FIG. 6F, the limiting structure 39 includes a wide tooth 53 which engages the threaded rod 26.

Figure 7:
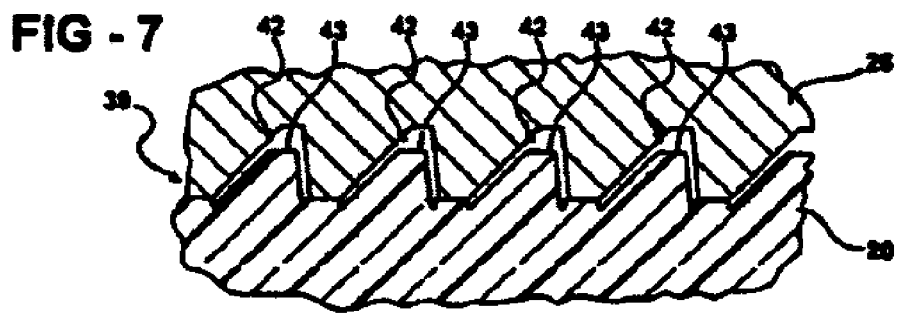
FIG. 7 is an enlarged perspective view of an alternative embodiment of the threads of the button of FIG. 4 in engagement with the threaded rod.

Two alternative threads 24 are shown in FIGS. 6A and 7. Both designs include the limiting structure 39, shown as the horizontal base 44. The threads 24 shown in FIG. 6 show a generally square design with the top 43 of the threads 24 being horizontal. The sides 45 of the threads 24 in FIG. 6 are angled slightly inward, e.g., 5°. Alternatively, the threads 24 shown in FIG. 7 also have a horizontal top 43, but the sides 45 of the threads 24 are angled greatly inward, e.g., 40° or 45° toward the top 43 of the threads 24. The opposite sides are angled slightly, e.g., 7°. The greatly inward angled sides 45 results in the threads 24 in FIG. 7 being generally A-shaped.

Additionally, the threads 24 of the rod 26 and/or the threads of the button 20 may be rounded.

It should be understood that the design of the threads 24, 27 is aimed at reducing the friction in actuating the apparatus and yielding a passageway for receiving steam. As such, modifications may be made to the designs herein described which do not depart from the spirit of the invention.

The cartridge dispensing mechanism 18 also includes first and second bushings 46A, 46B positioned on opposite sides of the button 20 at the axial bore 22. The bushings 46 slidably support the threaded rod 26.

Figure 9:
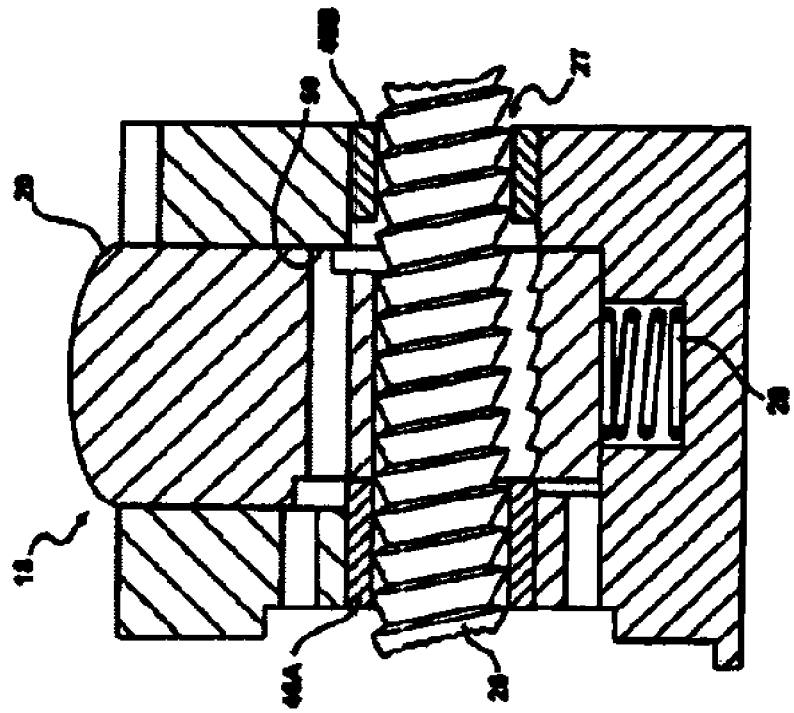
FIG. 9 is a cross-sectional view of the cartridge dispensing mechanism, with the button depressed, showing disengagement of the threaded rod for quickly priming the apparatus.

As shown, in FIGS. 1, 8 and 9, the button 20 includes a recessed flat surface 48. The first bushing 46A extends into the axial bore 22. This allows the button 20 to be inserted into the cartridge dispensing mechanism 18 in only one direction and ensures proper alignment thereof. The flat surface 48 engages the first bushing 46A as shown. This arrangement also prevents the button 20 from rotating within the cartridge dispensing mechanism 18 during priming and/or delivery.

The second bushing 46B is located near an interior surface 50 of the cartridge dispensing mechanism 18. The button 20 has a surface which is adjacent the second bushing 46B above and below the rod 26.

Referring to FIGS. 10 through 22, the cradle 14 defines a cylindrical bore 100 therein. Additionally, a keyed bore 102 is disposed in the button 20 and is linearly aligned with the cylindrical bore 100. In accordance with the embodiments discussed above, the threaded rod 26 is in threaded engagement with the axial bore 22 of the button 20 and extends into the axial cavity 16 of the cradle 14 wherein the button 20 is moveable into and out of threaded engagement with the threaded rod 26.

Figure 22:
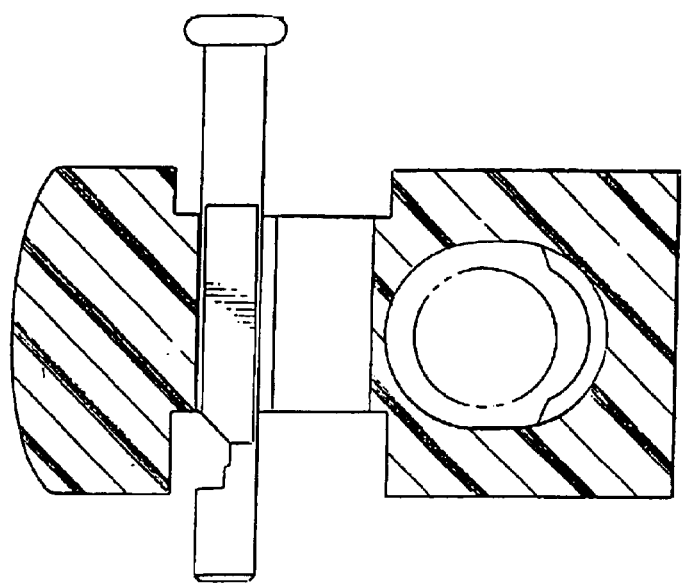
FIG. 22 is a cross-sectional view of the button and locking pin, according to the embodiment of FIG. 10.
Figure 21:
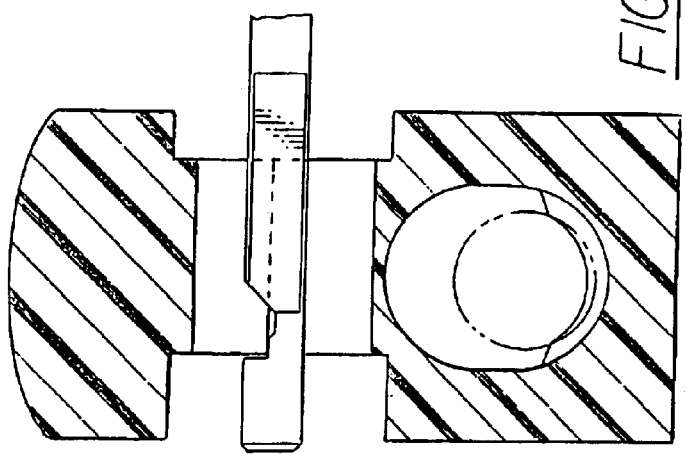
FIG. 21 is a cross-sectional view of the button and locking pin, according to the embodiment of FIG. 10.
Figure 20:
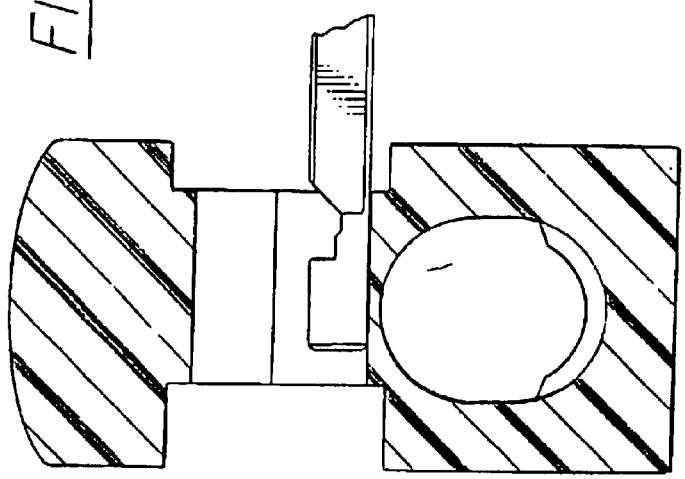
FIG. 20 is a cross-sectional view of the button and locking pin, according to the embodiment of FIG. 10.

Referring to FIGS. 20 through 22, a locking pin 104 is slideably disposed in both the cylindrical bore 100 and the keyed bore 102. The locking pin 104 is adapted to be moved from a first position (as shown in FIG. 21) to a second position (as shown in FIG. 22). More specifically, with the locking pin 104 in the first position, the button 20 may be moved out of threaded engagement with the threaded rod 26. Conversely, the locking pin 104 being in the second position prevents the button 20 from moving out of threaded engagement with the threaded rod 26.

Referring to FIGS. 13 through 16, the locking pin 104 includes a cylindrical body 110 having a shelf end 112 and a flat portion 114 disposed thereon. The shelf end 112 defines a cavity 115 having a biasing member 116 disposed therein and extending therefrom. The shelf end 112 further includes a first shelf 118 for disposing the button 20 thereon and engaging the button 20 and the threaded rod 26 in a static position relative to each other. The shelf end 112 yet further includes a second shelf 120 coupled to the first shelf 118 for disposing the button 20 thereon and engaging the button 20 and the threaded rod 26 in the static position relative to each other.

Referring to FIGS. 17 through 19, the keyed bore 102 includes a top end 122 for slideably engaging the flat portion 114 and allowing the button 20 to slideably engage the threaded rod 26. The keyed bore 102 further includes a beveled end 124 for receiving the shelf end 112, thereby engaging the threaded rod 26 in the static position relative to the button 20.

Referring back to FIGS. 13 through 16, the flat portion 114 defines a first flat side 126 for aligning the locking pin 104 with the cylindrical bore 100 and the top end 122.

Moreover, the flat portion 114 further defines a second flat side 128 for aligning the locking pin 104 with the cylindrical bore 100 and the top end 122.

Referring to FIGS. 19 through 21, in operation the cylindrical bore 100 and the keyed bore 102 are aligned such that the locking pin 104 is slideably engaged and biased outwardly from the cartridge 18. With reference to FIG. 19, while in the first position, the beveled end 124 of the keyed bore 102 resides on either the first shelf 118 or the second shelf 120, thereby preventing the button 20 from being depressed and moved out of the first position, while still allowing the threaded rod 26 to be advanced. Once the locking pin 104 is pushed inwardly toward the cartridge 18, the flat portion 114 aligns with the top end 122, thereby allowing the button 20 to be depressed and moved from the first position to the second position.

More specifically, with the locking pin 104 in the first position 106, the button 20 may not be moved out of threaded engagement with the threaded rod 26. Conversely, the locking pin 104 being in the second position 108 allows the button 20 to be in threaded engagement with the threaded rod 26. If the locking pin 104 is released while the button 20 is depressed, then biasing member 116 continues to urge the locking pin 104 outward from the cartridge 18. Simultaneously, the beveled end 124 of the keyed bore 102 travels over a ramp 130 to the first shelf 118 or the second shelf 120.

In practice, as the threaded rod 26 is advanced into the axial cavity 16, the forward pressure from the threaded rod 26 causes the bone cement to be released therefrom. Consequently, once forward pressure ceases, a reverse pressure is introduced into the axial cavity 16 which forces the threaded rod 26 to retreat out of the axial cavity 16. The locking pin 104 maintains threaded engagement of the button 20 with the threaded rod 26, thereby preventing reverse pressure from backing the threaded rod 26 out of the axial cavity 16.

Obviously, many modifications and variations of the present invention are possible in light of the above teachings. The invention has been described in an illustrative manner, and it is to be understood that the terminology that has been used is intended to be in the nature of words of description rather than limitation. It will be apparent to those skilled in the art that many modifications and variations of the present invention are possible in light of the above teachings. Therefore, it is to be understood that the invention may be practiced otherwise than as specifically described.

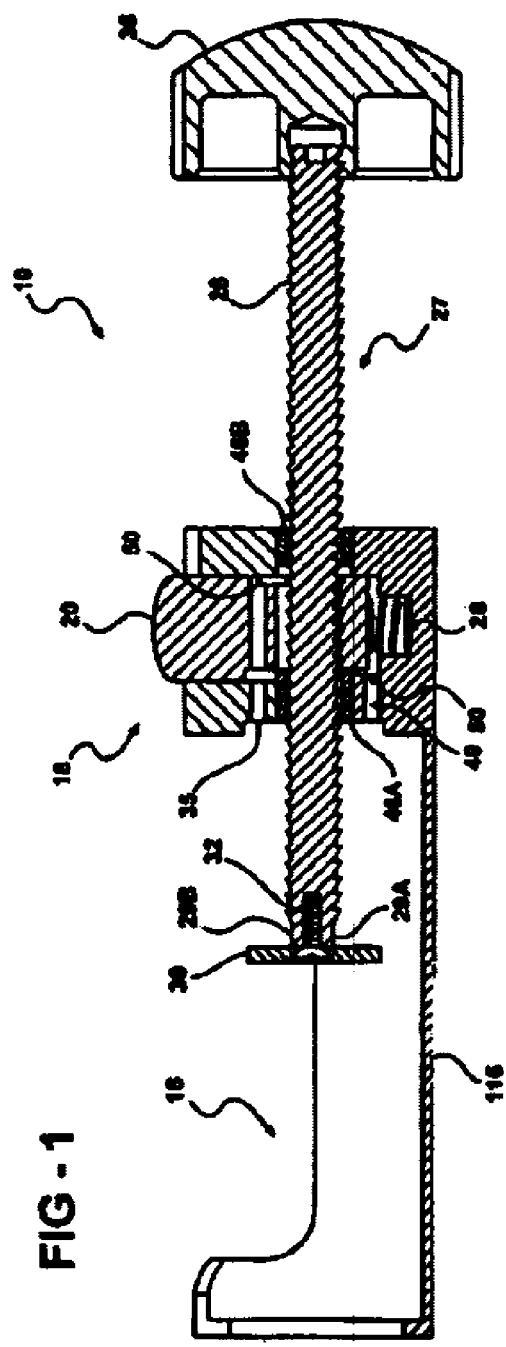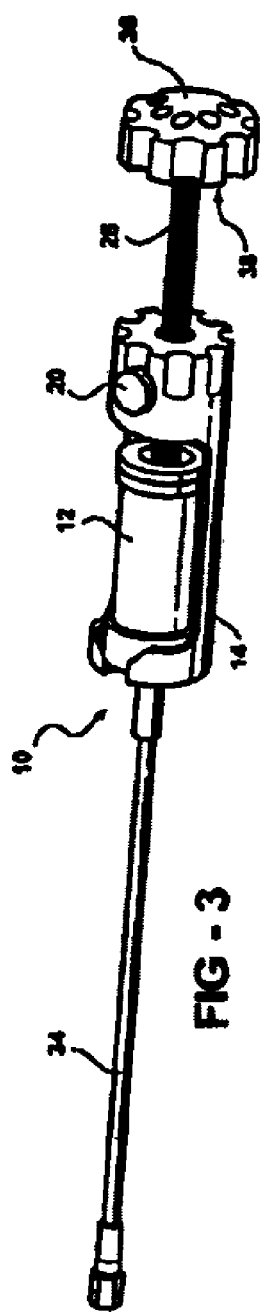

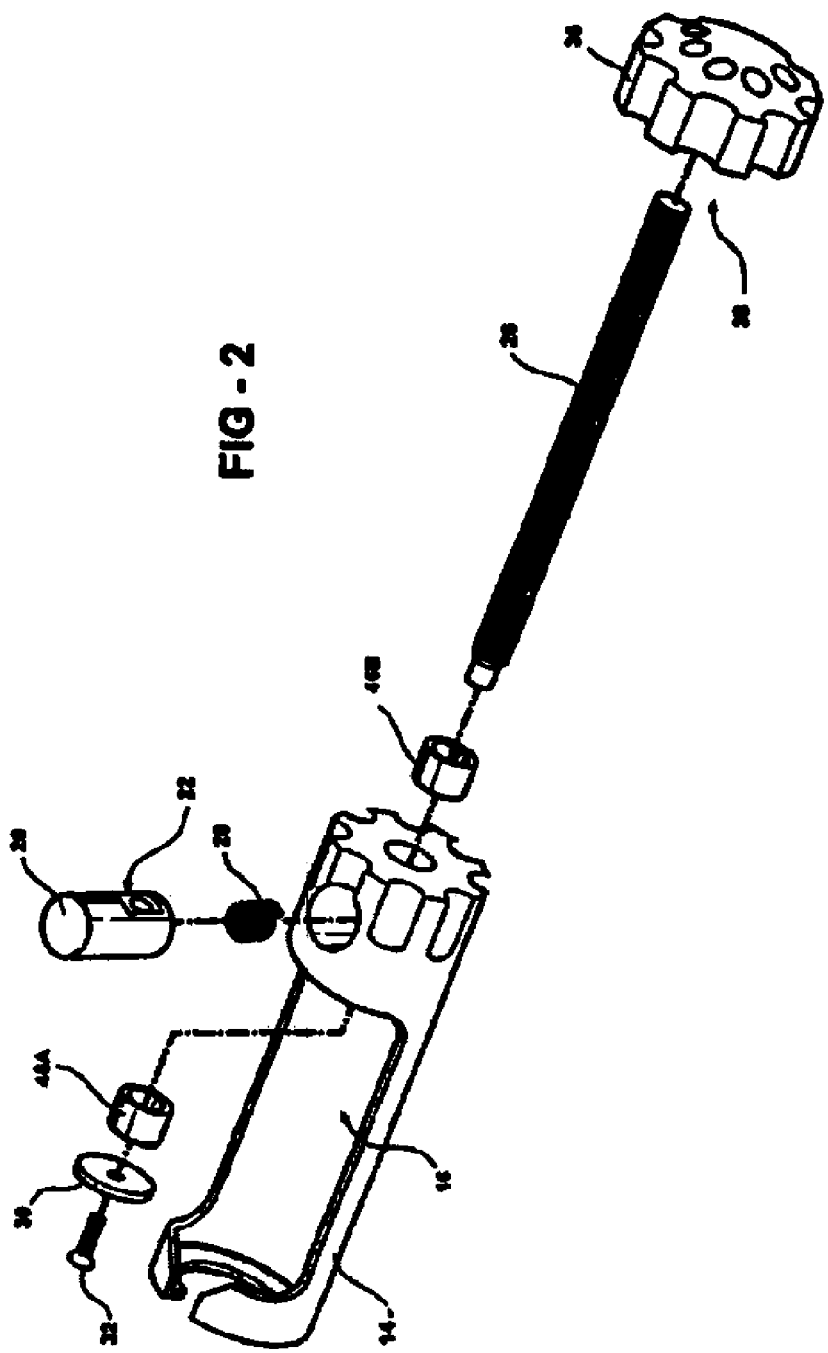

What is claimed is:

1. A delivery apparatus for injecting cement from a cartridge, the apparatus comprising:
   a cradle with an axial cavity extending therethrough for supporting the cartridge;
   a cartridge dispensing mechanism coupled to the cradle;
   a button having threads and defining an axial bore, the button being moveable into and out of threaded engagement;
   a threaded rod extending into the axial cavity of the cradle, the button being moveable into and out of threaded engagement with the threaded rod; and
   a locking pin slidably coupled to the cradle and the button and moveable between a first position and a second position, the button being moveable into and out of threaded engagement with the threaded rod when the locking pin is in the first position and the button not being moveable out of threaded engagement with the threaded rod when the locking pin is in the second position.

2. An apparatus, as set forth in claim 1, wherein the mechanism farther includes a first cleaning passageway defined by the cartridge delivery mechanism and extending from the exterior thereof to the threaded engagement of the rod.

3. An apparatus, as set forth in claim 1, wherein at least a portion of the threads of the button are spaced from the threaded rod to define a second cleaning passageway for conveying a cleaning medium therethrough.

4. An apparatus, as set forth in claim 1, wherein the axial bore of the button is adapted for moving the button between engaged and disengaged positions.

5. An apparatus, as set forth in claim 4, wherein the axial bore of the button has a diameter greater than a diameter of the threaded rod.

6. An apparatus, as set forth in claim 1, wherein the mechanism further includes a biasing device for biasing the threads of the button into the threaded engagement with the threaded rod.

7. An apparatus, as set forth in claim 1, wherein the mechanism includes bushings slidably supporting the rod.

8. An apparatus, as set forth in claim 7, wherein the button includes a flat surface for engaging one of the bushings to ensure proper alignment of the threads of the button when engaging the threaded rod.

9. An apparatus, as set forth in claim 1, wherein the threaded rod includes a first end and a second end, wherein the apparatus includes a disc attached to the first end of the threaded rod for advancing the ejection of cement from the cartridge.

10. An apparatus, as set forth in claim 9, wherein the mechanism includes a recess for receiving the disc.

11. An apparatus, as set forth in claim 9, including a handle attached to the second end of the threaded rod for manually rotating the threaded rod while in threaded engagement with the threads on the button thereby advancing the disc and ejecting cement from the cartridge.

12. An apparatus, as set forth in claim 11, wherein the handle includes markings for indicating degree of rotation thereof and for indicating the ejection of a predetermined amount of cement from the cartridge.

13. A delivery apparatus for injecting cement from a cartridge, the apparatus comprising:
   a cradle with an axial cavity extending therethrough for supporting the cartridge;
   a cartridge dispensing mechanism coupled to the cradle;
   a button having threads and defining an axial bore;
   a threaded rod having threads and being in threaded engagement with the axial bore and extending into the axial cavity of the cradle;
   a limiting structure for limiting a travel of the button and minimizing friction and pinching between the button and the threaded rod, the button being moveable into and out of threaded engagement with the threaded rod; and,
   a locking pin slidably coupled to the cradle and the button and moveable between a first position and a second position, the button being moveable into and out of threaded engagement with the threaded rod when the locking pin is in the first position and the button not being moveable out of threaded engagement with the threaded rod when the locking pin is in the second position.

14. A delivery apparatus, as set forth in claim 13, wherein the limiting structure includes at least one horizontal base formed between threads of the button, wherein a top edge of the threads of the threaded rod are in contact with the horizontal base while the button is in threaded engagement with the threaded rod.

15. A delivery apparatus, as set forth in claim 14, wherein the threads of the button are located on a bottom portion of the button.

16. A delivery apparatus, as set forth in claim 15, wherein the horizontal base extends over a portion of a width of the bottom portion of the button.

17. A delivery apparatus, as set forth in claim 13, wherein the limiting structure includes a stop.

18. A delivery apparatus, as set forth in claim 13, wherein the limiting structure includes at least one pin inserted through a bottom of the button between the threads of the button.

19. A delivery apparatus, as set forth in claim 13, wherein the limiting structure includes a wide tooth which engages the threaded rod.

20. A delivery apparatus for injecting cement from a cartridge, the apparatus comprising:
   a cradle with an axial cavity extending therethrough for supporting the cartridge;
   a cartridge dispensing mechanism coupled to the cradle and defining;
   a cylindrical bore therein;
   a button having threads and defining an axial bore;
   a keyed bore disposed in the button and being linearly aligned with the cylindrical bore;
   a threaded rod in threaded engagement with the axial bore of the button and extending into the axial cavity of the cradle wherein the button is moveable into and out of threaded engagement with the threaded rod; and
   a locking pin slideably disposed in both the cylindrical bore and the keyed bore for being moved from a first position to a second position.

21. A delivery apparatus, as set forth in claim 20, including the locking pin being in the first position for preventing the button from being moved out of threaded engagement with the threaded rod.

22. A delivery apparatus, as set forth in claim 21, including the locking pin being in the second position for allowing the button to be moved out of threaded engagement with the threaded rod.

23. A delivery apparatus, as set forth in claim 20, wherein the lacking pin includes a cylindrical body having a shelf end and a flat portion disposed thereon.

24. A delivery apparatus, as set forth in claim 23, wherein the shelf end defines a cavity having a biasing member disposed therein and extending therefrom.

25. A delivery apparatus, as set forth in claim 24, wherein the shelf end includes a first shelf for disposing the button thereon and engaging the button and the threaded rod in a static position relative to each other.

26. A delivery apparatus, as set forth in claim 25, wherein the shelf end includes a second shelf coupled to the first shelf for disposing the button thereon and engaging the button and the threaded rod in a static position relative to each other.

27. A delivery apparatus, as set forth in claim 26, wherein the keyed bore includes a top end for slideably engaging the flat portion and activating the button to slideably engage the threaded rod and a beveled end for receiving the shelf end thereby engaging the threaded rod in the static position relative to the button.

28. A delivery apparatus, as set forth in claim 27, wherein the flat portion defines a first flat side for aligning the locking pin with the cylindrical bore and the top end.

29. A delivery apparatus, as set forth in claim 28, wherein the flat portion defines a second flat side for aligning the locking pin with the cylindrical bore and the top end.

30. A delivery apparatus for injecting cement from a cartridge, the apparatus comprising:
   a cradle with an axial cavity extending therethrough for supporting the cartridge;
   a cartridge dispensing mechanism coupled to the cradle and defining
   a cylindrical bore therein;
   a button having threads and defining an axial bore;
   a keyed bore disposed in the button and being linearly aligned with the cylindrical bore;
   a threaded rod in threaded engagement with the axial bore of the button and extending into the axial cavity of the cradle wherein the button is moveable into and out of threaded engagement with the threaded rod;
   a locking pin slideably disposed in both the cylindrical bore and the keyed bore for being moved from a first position to a second position;
   a first cleaning passageway defined by the cartridge delivery mechanism and extending from the exterior thereof to the threaded engagement of the rod;
   threads disposed in the axial bore and being spaced from the threaded rod to define a second cleaning passageway for convey a cleaning medium therethrough;
   a biasing device for biasing the threads of the axial bore into threaded engagement with the threaded rod;
   a limiting structure for limiting travel of the button and minimizing friction and pinching between the button and the threaded rod; and
   bushings slidably supporting the threaded rod.

* * * * *

UNITED STATES PATENT AND TRADEMARK OFFICE
CERTIFICATE OF CORRECTION

PATENT NO. : 6,796,987 B2
DATED : September 28, 2004
INVENTOR(S) : Christopher M. Tague et al.

It is certified that error appears in the above-identified patent and that said Letters Patent is hereby corrected as shown below:

Delete Drawing Sheets 1-5 and replace with the attached drawing sheets 1-5 and delete drawing sheets 6-9.

Column 8,
Line 2, delete the word "farther" and replace with the word -- further --.

Column 10,
Line 41, delete the word "for" and replace with the word -- to --.

Signed and Sealed this

Twenty-second Day of November, 2005

JON W. DUDAS
*Director of the United States Patent and Trademark Office*